United States Patent
Würfel

(10) Patent No.: US 11,214,770 B2
(45) Date of Patent: Jan. 4, 2022

(54) POLAR BODY INJECTION

(71) Applicant: Wolfgang Würfel, Sixtnitgern (DE)

(72) Inventor: Wolfgang Würfel, Sixtnitgern (DE)

(*) Notice: Subject to any disclaimer, the term of this patent is extended or adjusted under 35 U.S.C. 154(b) by 476 days.

(21) Appl. No.: 15/767,045

(22) PCT Filed: Sep. 22, 2016

(86) PCT No.: PCT/EP2016/001588
§ 371 (c)(1),
(2) Date: Apr. 9, 2018

(87) PCT Pub. No.: WO2017/059946
PCT Pub. Date: Apr. 13, 2017

(65) Prior Publication Data
US 2018/0291338 A1 Oct. 11, 2018

(30) Foreign Application Priority Data

Oct. 9, 2015 (DE) .................... 10 2015 013 156.7

(51) Int. Cl.
*C12N 5/0735* (2010.01)
*C12N 5/075* (2010.01)

(52) U.S. Cl.
CPC ......... *C12N 5/0609* (2013.01); *C12N 5/0606* (2013.01); *C12N 2506/04* (2013.01)

(58) Field of Classification Search
CPC . C12N 5/0609; C12N 5/0606; C12N 2506/04
USPC ...................................................... 435/377
See application file for complete search history.

(56) References Cited

U.S. PATENT DOCUMENTS

| 6,143,564 | A * | 11/2000 | Wakayama | .................... 435/1.1 |
| 2003/0129745 | A1 | 7/2003 | Robl et al. | |
| 2014/0335619 | A1 | 11/2014 | Mitalipov et al. | |

FOREIGN PATENT DOCUMENTS

| DE | 10 2004 062184 A1 | 7/2006 |
| WO | 03/100018 A2 | 12/2003 |
| WO | 2004/003182 A2 | 1/2004 |
| WO | 2008/033469 A1 | 3/2008 |

OTHER PUBLICATIONS

Human Fertilization and Embryology Authority (HFEA) "Review of the Safety and Efficacy of Polar Body Transfer to Avoid Mitochondrial Disease"; Oct. 2014. (Year: 2014).*
Wakayama et al., Stem Cells. "Efficient Establishment of Mouse Embryonic Stem Cell Lines from Single Blastomeres and Polar Bodies", Apr. 2007; 25(4): 986-93. (Year: 2007).*
Ethics Committee of the Society of Reproductive Medicine, "Human somatic cell nuclear transfer (cloning)", 2000, Fertility and Stability 74(5), p. 873-876.*
Kono et al., "Birth of parthenogenetic mice that can develop to adulthood", 2004, Nature 428, p. 860-864.*
Reubinoff et al., "Embryonic stem cell lines from human blastocysts: somatic differentiation in vitro", 2000, Nature Biotechnology 16, p. 399-404.*
Wakayama et al., "The First Polar Body Can Be Used for the Production of Normal Offspring in Mice", 1998, Biology of Reproduction 59, p. 100-104.*
International Search Report for PCT International Patent Application No. PCT/EP2016/001588 dated Dec. 23, 2016.
Sayaka Wakayama et al: Efficient establishment of mouse embryonic stem cell lines from single blastomeres and polar bodies, Stem Cells, Alphamed Press, Dayton, OH, US, vol. 25, No. 4, Apr. 1, 2007 (Apr. 1, 2007), pp. 986-993, XP002635116, ISSN: 1066-5099, DOI: 10.1634/STEMCELLS. 2006-0615.
Ju J Y et al: "Establishment of stem cell lines from nuclear transferred and parthenogenetically activated mouse oocytes for therapeutic cloning", Fertility and Sterility, Elsevier Science Inc, New York, NY, USA, vol. 89, No. 5, May 1, 2008 (May 1, 2008), pp. 1314-1323, XP022668260, ISSN: 0015-0282, DOI: 10.1016/J.FERTNSTERT.2006.11.203.

* cited by examiner

*Primary Examiner* — Michael D Burkhart
(74) *Attorney, Agent, or Firm* — Quarles & Brady LLP

(57) ABSTRACT

The invention relates to a method for polar body injection, which comprises removing a polar body from a first egg cell and injecting the polar body into a second egg cell that is in a fertilizable state.

9 Claims, 6 Drawing Sheets

POLAR BODY INJECTION

CROSS-REFERENCE TO RELATED APPLICATIONS

This application represents the national stage entry of PCT International Application No. PCT/EP2016/001588 filed Sep. 22, 2016 and claims priority to German Patent Application No. 10 2015 013 156.7 filed Oct. 9, 2015. The contents of this application are hereby incorporated by reference as if set forth in their entirety herein.

TECHNICAL FIELD

The present invention relates to the general field of stem cell production and in particular a method for injecting a polar body into an egg cell.

BACKGROUND

Stem cells have the ability to produce a broad spectrum of different cell types by differentiation. Due to this ability to differentiate, there is an interest in the production and use of stem cells from a medical point of view, for example, to replace diseased or injured tissue.

Various methods of obtaining stem cells have raised ethical concerns, in particular with regard to the use of embryos.

PROBLEM DEFINITION

Against this background, the invention has the objective of providing methods for stem cell collection, without the use of embryos or embryonic stem cells.

BRIEF DESCRIPTION

This problem is solved by a method and stem cells according to the independent claims. The dependent claims describe preferred embodiments.

An inventive method comprises removing a polar body from a first egg cell and injecting the polar body into a second egg cell, which is in a fertile state.

In this context, the term "polar body" refers in particular to the so-called secondary polar body, which is formed with haploid chromosome set during the second cell division, meiosis II. If such a polar body is not removed in accordance with the invention, but initially remains in the egg cell, it can generally be ejected in the setting of meiosis II.

Here, in addition to the mature ovum ready to be fertilized, the term "egg cell" should describe at least the oocyte, which is maturing in the setting of oogenesis.

In particular, the term "fertile state" means that the egg cell (a) has matured to the ovum state and (b) has not yet been fertilized; furthermore, that this egg cell has already ejected its polar bodies. On the other hand, the fertilization of an egg cell results in the fact that it is generally capable of initiating the process of development of an organism, for example, a human being. The inventive method does not use raw materials or intermediates that would be suitable for initiating the process of development of an organism. In particular, the method does not use fertilized eggs. Also, neither male reproductive cells nor chromosomes or genomes of male origin are used. Instead, by injecting the polar body into the second egg cell, it is, for example, possible that a unimaternal disomy of all chromosomes develops, which according to current findings is not capable of developing into a viable organism.

In particular, it is provided that the removal of the polar body and the injection of the polar body are carried out in vitro. In such embodiments, the first egg cell can have been removed from a first individual. The second egg cell can have been taken from the first individual or from a second individual. The removal of the first egg cell from a first individual, and the removal of the second egg cell from the first individual or from a second individual, can be covered by embodiments of the inventive method.

In general, the egg cells can have been removed from any organism. In some embodiments, the first egg cell and the second egg cell can be human egg cells.

In some embodiments, the first egg cell and the second egg cell can be the same egg cell. Preferably, the method between removing the polar body and injecting the polar body into the same egg cell can comprise allowing for a period of rest. Alternatively, the first egg cell and the second egg cell can involve two separate egg cells.

In general, the removal of a polar body from the first egg cell can comprise at least fixation of the first egg cell, opening of the first egg cell and/or aspiration of the polar body from the first egg cell.

In general, the injection of the polar body can be performed in intracytoplasmic manner. The term "intracytoplasmic injection" describes an injection into the interior of the cytoplasm. By means of intracytoplasmic injection, the polar body is brought into proximity of the chromosomes of the second egg cell.

Alternatively, or additionally, the injection of the polar body (i) can comprise depositing the polar body between the zona pellucida of the second egg cell and the cytoplasm of the second egg cell, and (ii) fusing the membranes, for example, by means of electrofusion. Preferably, a polar body ejected from the second egg cell was removed at least prior to fusing the membranes. As a result of electrofusion, the content of the injected polar body, in particular the chromosomes it contains, can enter the cytoplasm and thus the proximity of the chromosomes of the second egg cell.

In general, the method can also comprise lysing, i.e., causing a lysis, of the polar body. In particular, lysing of the polar body can take place between its removal and injection. In this case, the lysed polar body is injected instead of the intact polar body. Subsequently, the term "lysed polar body" shall describe at least the lysate of the polar body. In particular, the lysed polar body comprises the chromosomes of the removed polar body. In general, it is possible to use an injection pipette with low diameter for the injection of the lysed polar body, even if in some embodiments it would not be possible to inject the removed polar body in an intact state with the small diameter injection pipette. In preferred embodiments, the lysing of the polar body can be performed in osmotic manner. For this purpose, the polar body can be placed in a hypoosmolar solution. For example, the hypoosmolar solution can be kept under oil seal. Thus, by means of osmosis, the polar body can be made to "burst", i.e., it can result in lysis. When adding the hypoosmolar solution into the injection pipette, the lysed polar body can also be inserted in the injection pipette.

In general, the method can also comprise culturing the second egg cell until a blastocyst is formed and isolating at least one stem cell from the blastocyst. Preferably, the at least one stem cell can be isolated from an inner cell mass of the blastocyst. For example, the isolation of at least one stem cell from a blastocyst is shown in the patent specification DE 10 2004 062 184 B4. In general, the at least one isolated stem cell can involve an embryonic stem cell.

In addition, these embodiments can comprise the differentiation of at least one stem cell. In particular, the differentiation of the at least one stem cell can comprise forming tissue as a result of stimulation. Stimulation can involve that one or multiple factors, such as chemical reagents or messenger substance, are present or absent.

Furthermore, the invention provides one or multiple stem cells, which was/were obtained by an inventive method. In particular, these stem cell(s) can be available in pluripotent state.

BRIEF DESCRIPTION OF THE DRAWINGS

In the following description of embodiments of the invention, reference is made to the attached drawings, which show.

DETAILED DESCRIPTION

Figure 1:
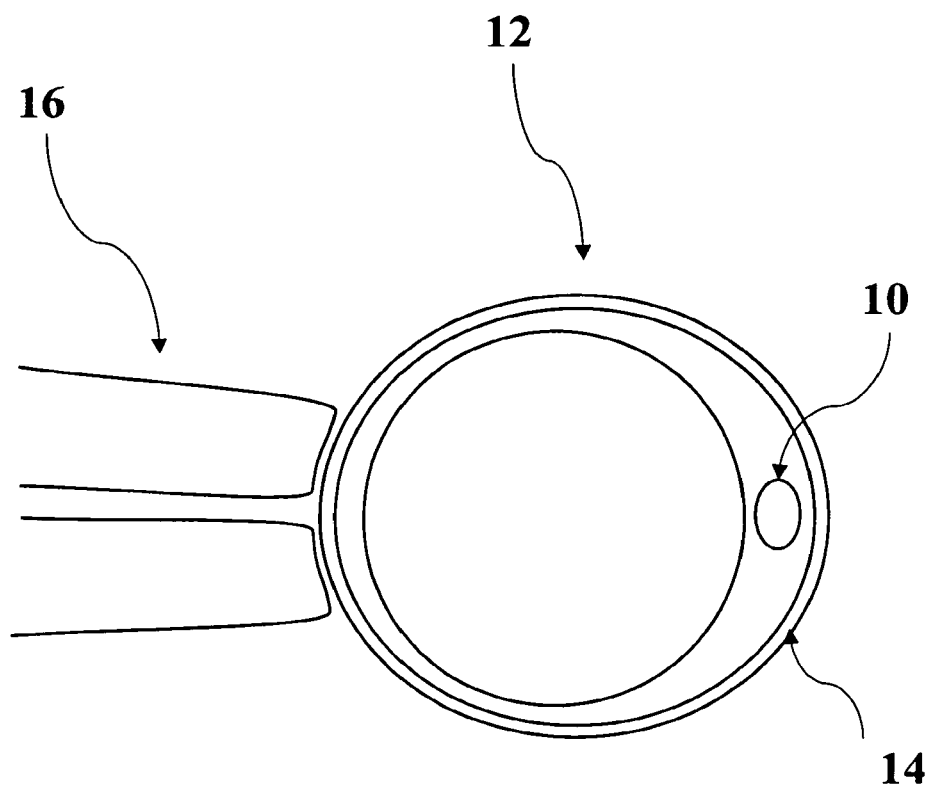
FIG. 1 shows a schematic representation of a first egg cell prior to removing the polar body.

FIG. 1 shows a schematic representation of a first egg cell 12 prior to removing the polar body 10. The first egg cell 12 is fixed by means of a holding pipette 16. In the present case, the holding pipette 16 was introduced to the first egg cell 12 from the left side shown in the representation, and the first egg cell was rotated to the extent that the polar body 10 is located on the right side of the first egg cell 12 shown in the representation. Among other things, the first egg cell comprises a plasma membrane 14, which also encloses the polar body 10.

Figure 2:
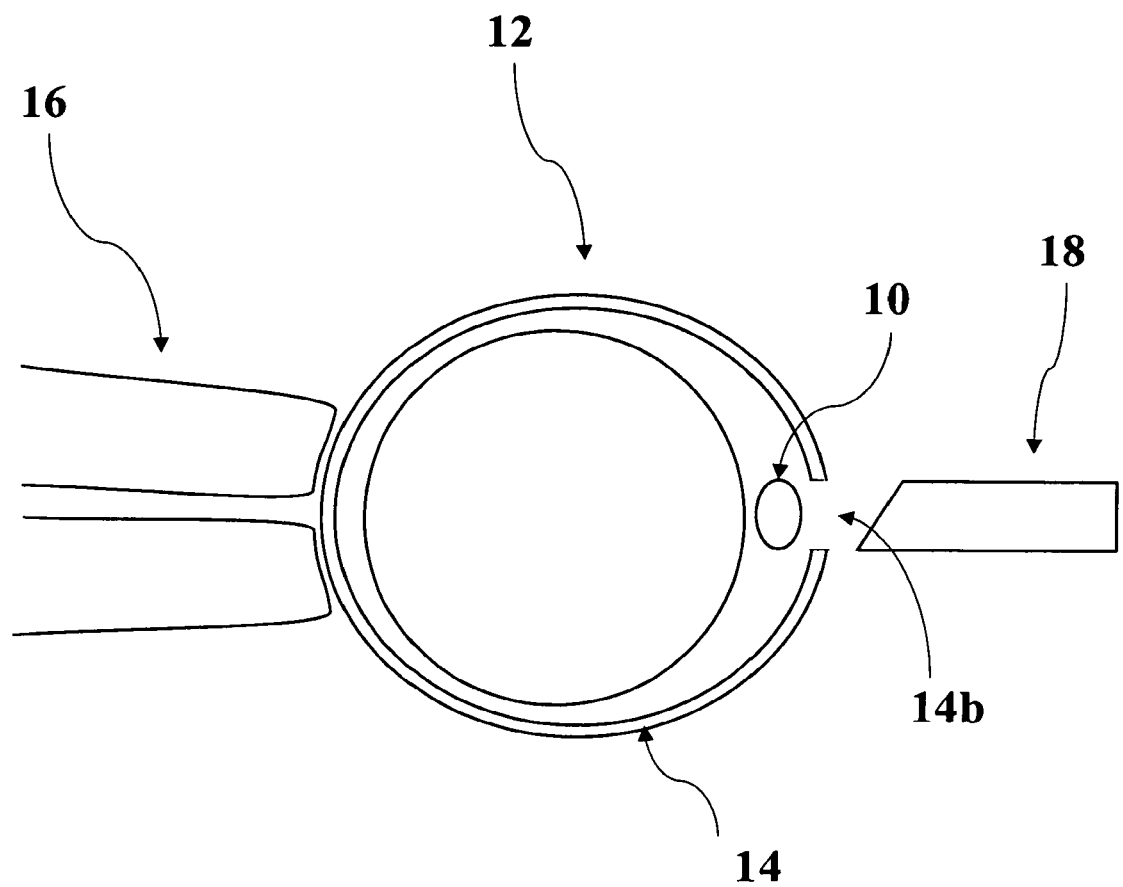
FIG. 2 shows a schematic representation of a first egg cell during the removal of the polar body.

FIG. 2 shows a schematic representation of a first egg cell 12 during removal of the polar body 10. In particular, this can involve the egg cell 12 shown in FIG. 1. The plasma membrane 14 of the first egg cell 12 has an opening 14b, which was produced, for example, by means of a laser. The opening 14b is located in the proximity of the polar body 10, and a biopsy pipette 18 can be inserted through the opening 14b. The biopsy pipette 18 shown is positioned directly prior to insertion into the opening 14b. The biopsy pipette 18 is used to aspirate the polar body and thus remove it from the first egg cell 12. After removal, the polar body can be stored in the culture medium until further use.

Figure 3:
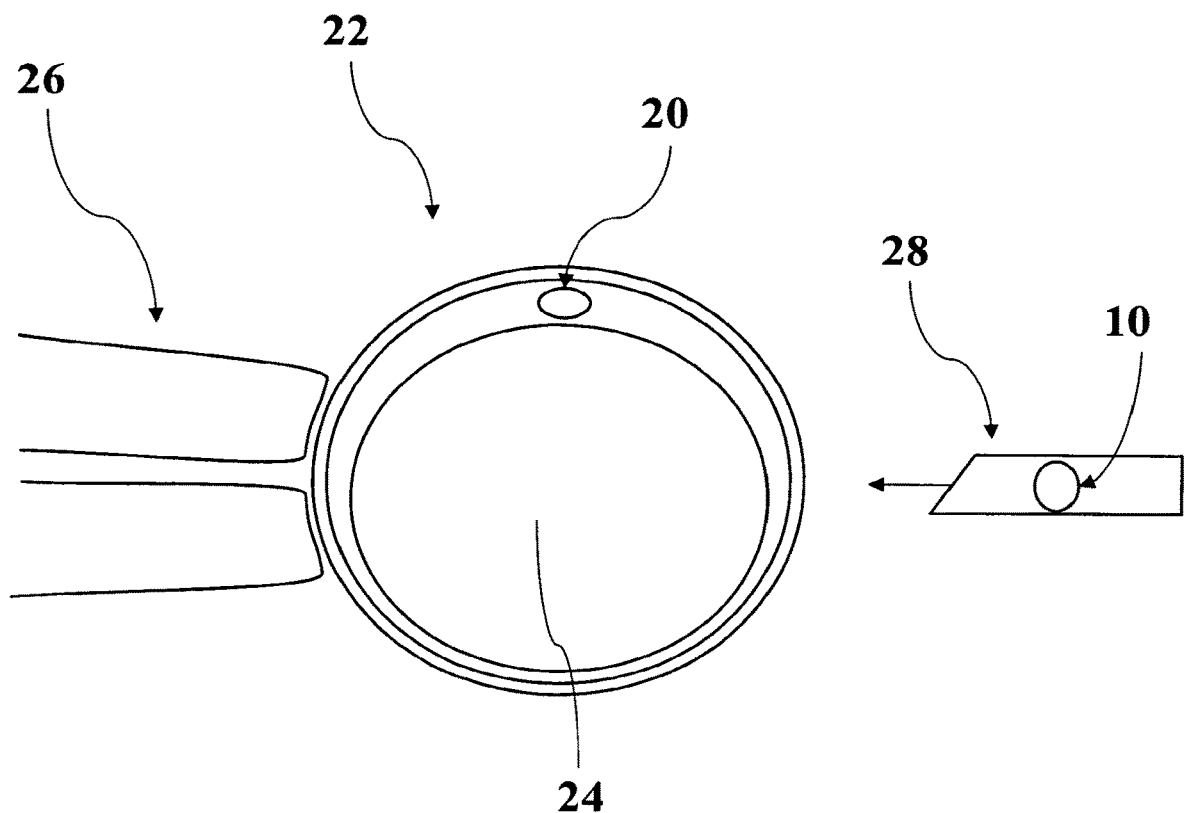
FIG. 3 shows a schematic representation of a second egg cell shortly before injecting a polar body.

FIG. 3 shows a schematic representation of a second egg cell 22 just prior to injecting a polar body 10. For example, the polar body 10 can be removed from a first egg cell 12, as shown in FIG. 1 and/or FIG. 2. Among other things, the second egg cell 22 comprises a cytoplasm 24. The polar body ejected by the second egg cell 22 during its maturation has the reference symbol 20. In the present case, said polar body is preferably located in the representation at the upper edge ("at 12 o'clock") or at the lower edge ("at 6 o'clock") to avoid that the spindle of the second egg is damaged by an injection pipette. However, the presence of this ejected polar body is not mandatory. In some embodiments, the polar body can be injected into the same egg cell from which it was taken. In these cases, the same egg cell has no further polar body after its polar body has been removed.

The second egg cell is fixed by means of a holding pipette 26. In the present case, the egg cell is fixed on the left side shown in the representation. For example, the polar body 10 can be injected from the right side shown in the representation. The polar body 10 has already been inserted into an injection pipette 28. For example, it may have been absorbed from a culture medium in which it was stored after being removed from a first egg cell. The injection pipette 28 is used to rupture the plasma membrane of the second egg cell 22 and to protrude into the cytoplasm 24. Then the polar body 10 can be deposited in the cytoplasm 24 by means of the injection pipette 28.

Figure 4:
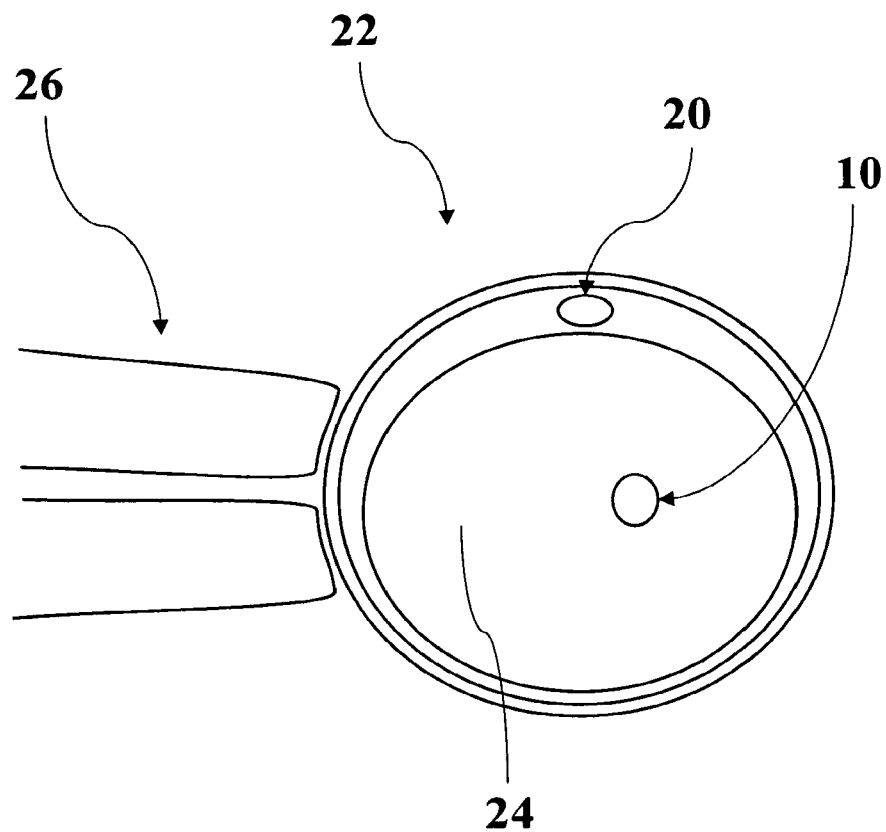
FIG. 4 shows a schematic representation of a second egg cell after injecting a polar body.

FIG. 4 shows a schematic representation of a second egg cell 22 after intracytoplasmic injection of a polar body 10. The second egg cell is fixed by means of a holding pipette 26. The polar body 10 is located inside the cytoplasm 24. The second egg cell 22 and the polar body 10 each have a haploid set of chromosomes (not shown). By fusing these two sets of chromosomes, a diploid set of chromosomes is created. Both sets of chromosomes are of maternal origin, there is no paternal set of chromosomes. Therefore, no fusion of paternal and maternal chromosomes takes place. If both the first egg cell and the second egg cell are removed from a first individual, the diploid cell involves a unimaternal disomy.

Figure 5:
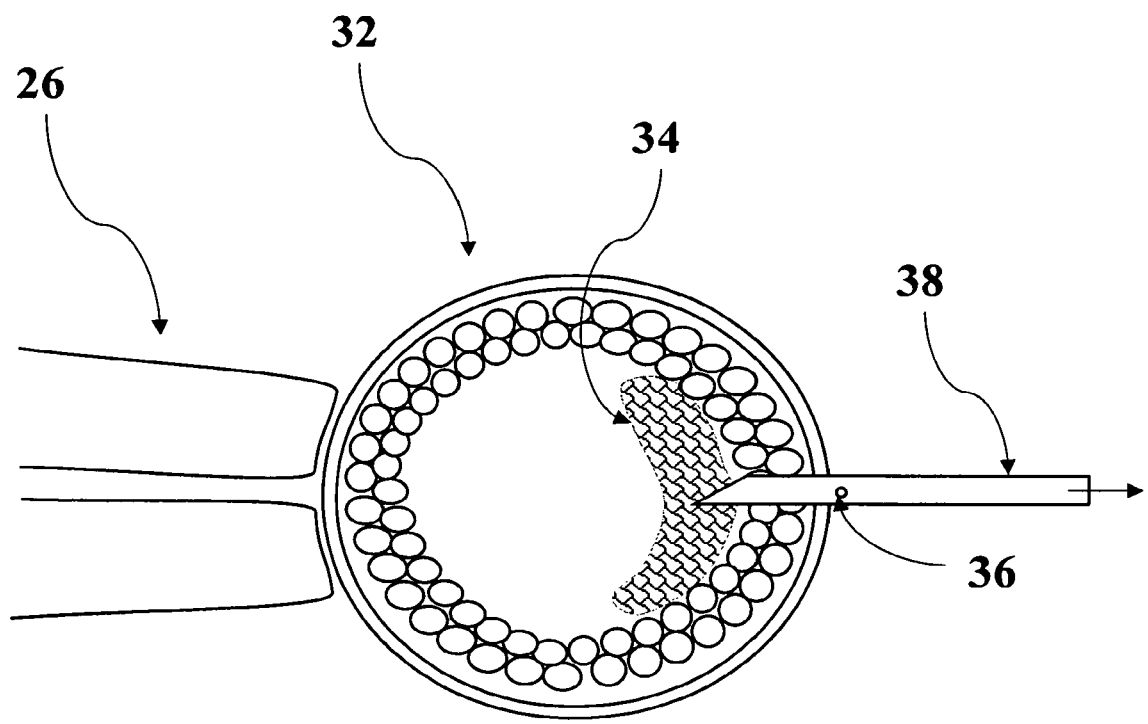
FIG. 5 shows a schematic representation of a second egg cell matured to a blastocyst during the removal of a stem cell.

FIG. 5 shows a schematic representation of a blastocyst 32. The blastocyst 32 shown has matured from a second egg cell after a polar body removed from a first egg cell has been injected into the second egg cell. The blastocyst 32 is fixed by means of a holding pipette 26. Among other things, the blastocyst 32 comprises an inner cell mass 34. By means of a pipette 38, at least one stem cell 36 can be removed from the inner cell mass 34 and isolated. Subsequently, the at least one isolated stem cell can be stimulated for differentiation, for example, to generate tissue for medical purposes.

Figure 6:
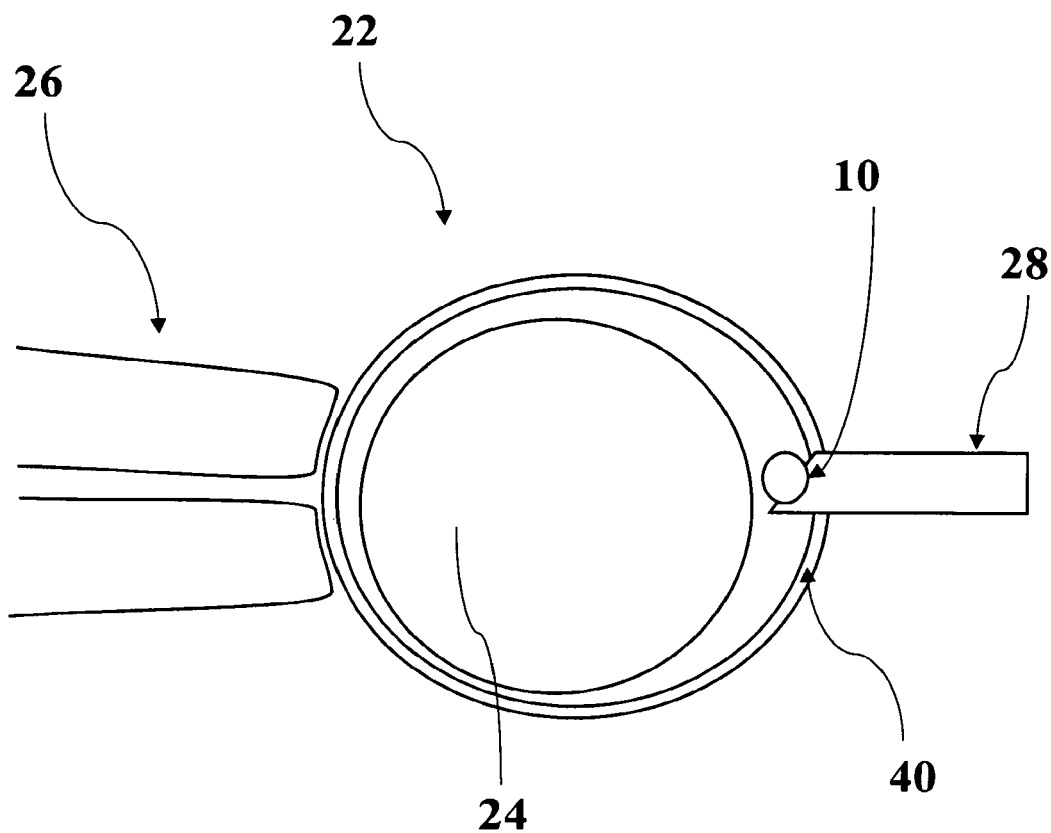
FIG. 6 shows a schematic representation of a a further embodiment of a second egg cell during the injection of a polar body.

FIG. 6 shows a schematic representation of a further embodiment of a second egg cell 22 during the injection of a polar body 10. The second egg cell 22 comprises a cytoplasm 24 and a zona pellucida 40. In the embodiment shown, the polar body is deposited between the zona pellucida 40 of the second egg cell 22 and the cytoplasm 24 of the second egg 22, using an injection pipette 28.

Thereupon, the membrane surrounding the cytoplasm 24 and the membrane surrounding the polar body can be stimulated to fuse. Preferably, this takes place by means of electrofusion. As a result of electrofusion, the content of the injected polar body 10, in particular the chromosomes contained (not shown), enters the cytoplasm 24 of the second egg cell 22. In the present embodiment, in contrast to the embodiment shown in FIG. 3, a polar body ejected from the second egg cell 22 was first removed, and the polar body 10 was placed in its position.

EXAMPLES

A first human egg cell in the oocyte stage is fixed under a stereomicroscope by means of a holding pipette (suction cannula with an outer diameter of approx. 100 μm, inner diameter of approx. 20 μm). The fixation is performed in such a way that the polar body of the first human egg cell is located on the right hand, at 3 o'clock in top view. By means of a laser (for example, infrared laser, especially at 1.48 μm), an opening in the zona pellucida is created at this point. The polar body is aspirated with a biopsy pipette (outer diameter approx. 15 µm, inner diameter approx. 13 µm). The polar body is placed in a culture drop in the same culture dish.

A second human egg cell, which is in the mature ovum stage, is fixed under the stereomicroscope by means of a holding pipette. Using an injection pipette, the polar body is aspirated, the plasma membrane is ruptured, and the polar body is deposited deep in the cytoplasm of the second human egg cell. The injection pipette is pulled back. The second human egg cell is cultured according to protocols known to experts from the field of in vitro fertilization or intracytoplasmic sperm injection (ICSI).

After cultivation of the second human egg cell up to the blastocyst stage, a stem cell is isolated from the blastocyst according to the method disclosed in the patent specification DE 10 2004 062 184 B4.

What is claimed is:

1. A method for stem cell production, comprising:
   (a) removing a secondary polar body from a first, unfertilized egg cell, wherein the secondary polar body comprises a haploid set of chromosomes,
   (b) injecting the secondary polar body into a second egg cell,
      wherein the second egg cell, immediately prior to secondary polar body injection:
      (i) has matured to the ovum state and is in a fertile state;
      (ii) is not the first egg cell;
      (iii) comprises a haploid set of chromosomes of maternal origin within its cytoplasm;
      (iv) has ejected its secondary polar body or has had its secondary polar body removed; and
   wherein after injection of the secondary polar body from the first egg cell, the second egg cell comprises a diploid set of chromosomes of maternal origin only and comprises no paternal chromosomes; and
   (c) cultivating the second egg cell up to the formation of a blastocyst.

2. A method according to claim 1, comprising:
   removing the first egg cell from a first individual,
   removing the second egg cell from the first individual or from a second individual.

3. A method according to claim 1, in which the first egg cell and the second egg cell are each human egg cells.

4. A method according to claim 1, also comprising:
   isolating at least one stem cell from the blastocyst.

5. A method according to claim 4, also comprising:
   differentiating the at least one stem cell.

6. A method according to claim 1, in which the removal of the secondary polar body comprises at least one of the following steps: fixing the first egg cell, opening the first egg cell, aspirating the secondary polar body from the first egg cell.

7. A method according to claim 1, in which the injection of the secondary polar body is performed in intracytoplasmic manner.

8. A method according to claim 1, the method comprising lysing of the secondary polar body prior to injection into the second egg cell.

9. The method of claim 8, wherein lysing comprises osmotic lysing.

* * * * *